US00PP20645P3

(12) United States Plant Patent
Khayat

(10) Patent No.: US PP20,645 P3
(45) Date of Patent: Jan. 12, 2010

(54) BANANA PLANT NAMED 'ADI'

(50) Latin Name: *Musa acuminata*
Varietal Denomination: Adi

(75) Inventor: Eli Khayat, Neve Ziv (IL)

(73) Assignee: Rahan Meristem (1998) LTD, Kibbutz Rosh Hanikra ( * ) Notice: Subject to any disclaimer, the term of this patent is extended or adjusted under 35 U.S.C. 154(b) by 0 days.

(21) Appl. No.: 12/074,275

(22) Filed: Mar. 3, 2008

(65) Prior Publication Data

US 2009/0222959 P1 Sep. 3, 2009

(51) Int. Cl.
*A01H 5/00* (2006.01)

(52) U.S. Cl. ..... Plt./160

(58) Field of Classification Search ..... Plt./160
See application file for complete search history.

(56) References Cited

OTHER PUBLICATIONS

1. Heslop Harrison and Trude Schwarzacher, "Domestication, genomics and the future for banana", Annals of Botany, 2007, vol. 100; pp. 1073-1084.

2. Khayat, Duvdevani, Lahav, Ballesteros, "Somaclonal variation in banana (*Musa acuminata* cv. Grand Nain) genetic mechanism, frequency, and application as a tool for clonal selection", 2004, "In banana improvement, cellular, molecular biology and induced mutations", pp. 97-109, Science Publishers Inc. Enfield NH, USA, Plymouth UK.

3. Emile Vanhandle, "Direct micro determination of sucrose", Analytical Biochemistry, vol. 22; pp. 280-283.

4. Khayat and Zieslin, "Effect of night temparature regimes on the assimilation, transport and metabolism in rose plants", 1986, Physiologia Plantarum, vol. 67; pp. 608-613.

*Primary Examiner*—Susan B McCormick Ewoldt
(74) *Attorney, Agent, or Firm*—KK Patents LLC; Lyn R Marantz

(57) ABSTRACT

Adi is a selection of the ancestral banana line Zelig, which belongs to *Musa acuminata* cv. Cavendish. When compared to its ancestral line, 'Adi' shows the following characteristics:

1. Dwarf-like stature,
2. Wider girth size,
3. Higher fruit yield,
4. Longer fruit size ("fingers"),
5. Higher levels of sucrose and starch in the pulp,
6. Tolerance to windy conditions.

4 Drawing Sheets

*Musa acuminata* (AAA) variety Cavendish 'Adi'.

'Adi' is a triploid banana plant belonging to *Musa acuminata* (AAA) variety Cavendish (not patented). 'Adi' is a mutant of the earlier selection 'Zelig' (not patented) originating in the Western Galilee, Israel. 'Zelig' is a sub-variety of the variety Cavendish that was found in the Western Galilee in the beginning of the 1980's. The 'Zelig' selection is known as a very unstable selection especially when propagated by tissue culture. The height of the 'Zelig' clone averages 3.5 meters. This mutant was created by an extensive process of tissue culture. The retro-transposing element expression was used as a marker in the selection process (ii). The Adi line was primarily selected on the basis of its short plant stature, and secondarily for its fruit having a higher fruit yield per stem, a longer finger size, as well for the fruits having a higher sucrose content in the pulp.

'Adi' was created using the tissue culture technology as is specified below.

i. A meristem was harvested from a 'Zelig' shoot that reached the height of 45 cm from the ground. The meristem was disinfected by immersion in 0.3% commercial sodium hypochlorite solution for 30 minutes, followed by several rinses with sterile distilled water. The disinfection process was repeated 3× as above and subsequently the meristems (0.5×0.5 cm) were placed on a solid medium containing MS salts, 0.03% w/v sucrose, 10 mg.$L^{-1}$ benzyladenine, and MS vitamins (multiplication medium).

ii. The meristems were incubated for 4 weeks at 22° Celsius under florescent lighting at a regime of 16/8 dark/light hours. The meristems were each subdivided longitudinally into 3 sub-meristems that were each cultured separately. Each of the 9 sub-meristems was incubated for an additional 4 weeks in conditions as described above.

iii. Following 24 subcultures as indicated in step ii., the subcultured meristems were transferred onto a medium that contained MS salts, 0.1 mg.$L^{-1}$ kinetin, MS vitamins, and 0.1 mg.$L^{-1}$ 1-naphthaleneacetic acid (NAA) (rooting and regeneration medium).

iv. After 4 weeks of culture in the rooting and regeneration medium, under the environmental conditions indicated in step ii., the plants were individually placed in 10 $cm^3$ peat moss plugs in a greenhouse under mist irrigation. After an additional 4 weeks of growth, each plant was placed in a 5 L pot and let grow until it reached the height of about 60 cm.

v. At 60 cm in height, the plants were removed from the pots and planted in the field in Kibbutz Rosh Hanikra Western Galilee, Israel, at a density of approximately 1200 plants per 1000 $m^2$.

vi. One single plant, which was named, was 'Adi' was selected from a population of 20,000 plants produced as described above in [002] steps i. through vi. The entire process of tissue culture was repeated on one of the meristems that was harvested from the 'Adi' plant, with the exception that the number of subcultures on the multiplication medium was reduced to 6 instead of the 24 indicated above.

vii. Following the multiplication of the 'Adi' meristem, a new population of 'Adi' was produced and placed in the field. This population was examined for the parameters that 'Adi' was selected for. This process was repeated 3× until a population of 10,000 plants was reached that did not deviate more than 10% in the selection characteristics. The selection characteristics deviating less than 10% confirmed the stability of 'Adi'.

BACKGROUND OF THE INVENTION

The 'Adi' selection was performed at Rosh Hanikra, the Western Galilee, Israel; by mutating an earlier selection known as 'Zelig', in 2001–2002. The mutation resulted as a consequence of multiple subcultures in vitro. In this case, there were 24 subcultures, which is an extremely high number of cycles of multiplications. This type of mutation known as somaclonal variation is induced by an extensive process of tissue culture (ii).

Banana and plantains (*Musa* spp.) comprise major food sources for more than 400 million people world wide (i). Of the huge volume of fruit production approximately 15% is exported to remote markets. Most banana and plantains are inter or intra hybrids between two species namely *Musa acuminata* (A genome) and *Musa balbisiana* (B genome). By far, the most important export variety is Cavendish (a triploid AAA). In the 1950's, this variety replaced "Gros Michel" (not patented) which was almost wiped out due to attacks from a new race of the fungal disease, *Fusarium* Wilt. Being resistant to the disease combined with wide consumer acceptance in export markets made 'Cavendish' irreplaceable. Due to double sterility and the triploid nature of 'Cavendish', breeders have very limited tools to improve the germplasm of this variety. Consequently, 'Cavendish' bananas suffer from a variety of pests and diseases. In addition, the plants are wind sensitive, have a relatively high stature, short shelf life of the fruit and low tolerance to environmental stresses like lack of or excess water, low mineral nutrition, soil compaction and salinity. Due to the inability of 'Cavendish' to cross hybridize there are very limited sources of variability.

Based on somaclonal variation, breeders have selected preferred clones that exhibit better traits in the offspring in comparison to the wild type. Given that these chromosomal changes do not involve recombination events, they are rare and restricted to a narrow range of phenotypic variations. Even with extensive tissue culture cycling, the rate of variation is entirely unpredictable. Nevertheless, some selected clones are highly desired by banana farmers due to their high performance, mainly in terms of yield and plant architecture. Among the most popular selections 'Gal' (U.S. patent application Ser. No. 12/042,177 continuation of Ser. No. 11/021,937) and 'Jaffa' (U.S. patent application Ser. No. 12/042,177 continuation of Ser. No. 11/021,937) are widely used throughout the world. These last two selections were achieved using a unique genetic tool that has been developed to validate high enough levels of mutations in the "in vitro" processed material (ii). This discovery was achieved through elucidation of a mode of mutation that involves expression of a reto-transposing element known as BanR1 element.

The plant 'Adi' that was developed by the inventor was derived from the 'Cavendish' selection 'Zelig'. The parameters used for the selection of 'Adi' were low stature and wide girth size. Despite its low stature, 'Adi' is characterized as a 'Cavendish' with high bunch weight and long fingers. In addition, starch and sucrose content in 'Adi' are higher than its originator line Zelig, and also higher than the other known Cavendish selections of 'Grand Nain' (not patented) and 'Williams' (not patented). An advantage of 'Adi''s low stature is easier accessibility to the petiole at harvest time. Easier accessibility to the bunch frees the farm workers from climbing on ladders to reach the bunch. In addition, airplane spraying is a problem in highly populated areas due to the dense population and buildings in the spraying area. 'Adi''s low stature facilitates hand or ground machinery spraying and so avoids the need for airplane spraying. Finally, 'Adi' is more tolerant to windy conditions than other Cavendish selections.

The mutant was derived by applying stressful tissue culture conditions for a long duration of 24 cycles in culture. Each cycle comprised a one-month duration. Due to its predetermined genetic instability, the 'Zelig' line was utilized as an originator of the new selection. 'Zelig' is known for its high rate of spontaneous mutations in the field.

This new selection of dessert banana plant, was asexually reproduced by corms in tissue culture by the inventor in Rosh Hanikra, Israel. Unlike its originator line 'Zelig', 'Adi' has been proven stable in the field for at least three consecutive generations.

CHARACTERISTICS OF THE NEW VARIETY

Figure 1:
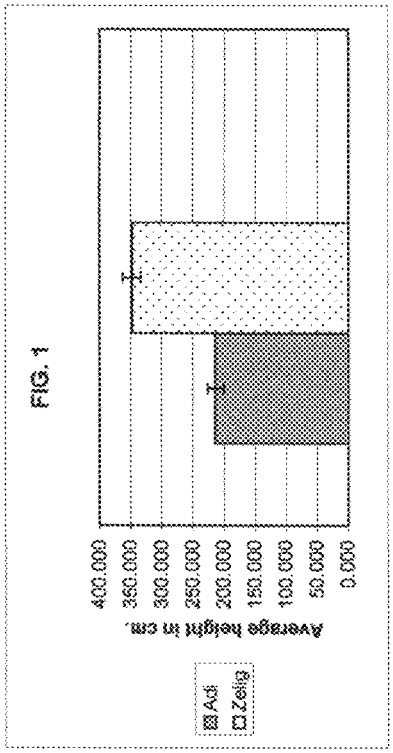
FIG. 1 shows average height (cm) of 'Adi' and 'Zelig' banana plants.
Figure 2:
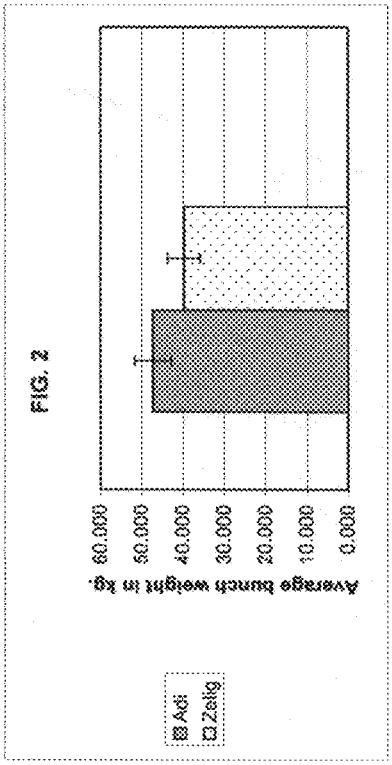
FIG. 2 shows average bunch weight (kg) of 'Adi' and 'Zelig' banana fruit.
Figure 3:
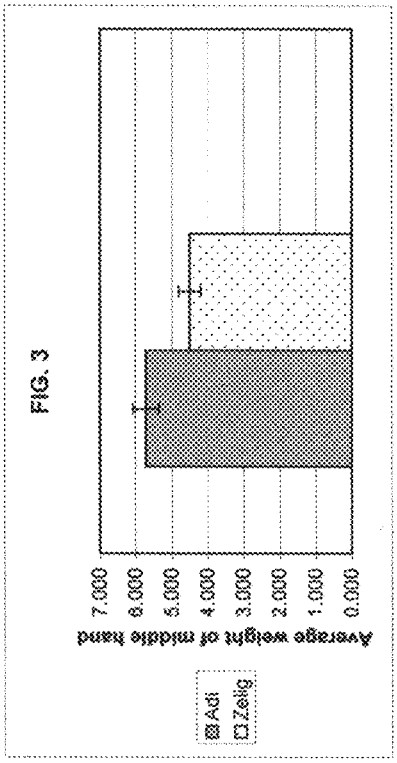
FIG. 3 shows middle hand average weight (kg) of 'Adi' and 'Zelig' banana fruit.
Figure 4:
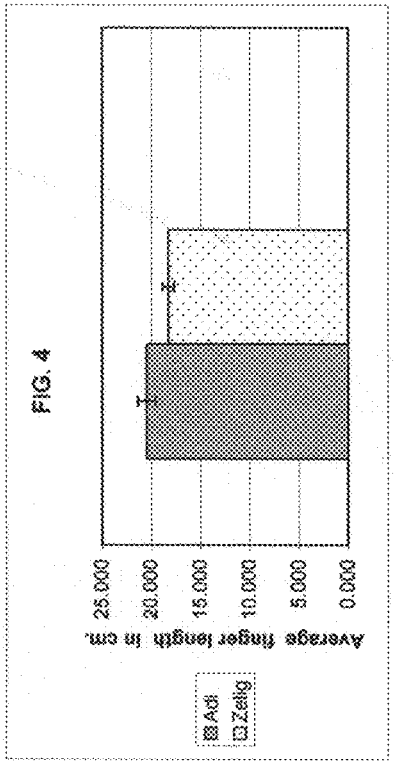
FIG. 4 shows average finger length (cm) of 'Adi' and 'Zelig' banana fruit.
Figure 6:
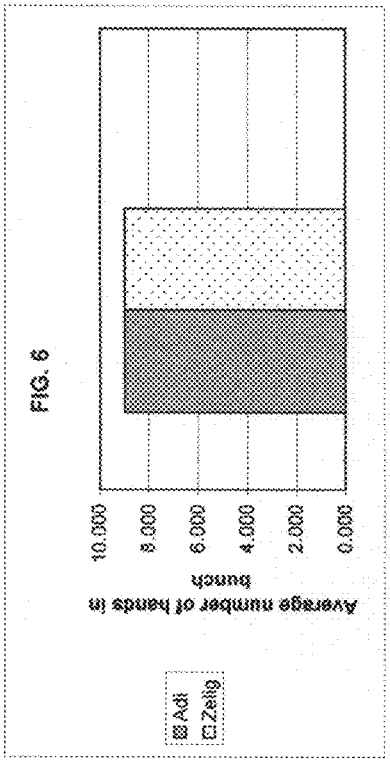
FIG. 6 shows average number of hands of 'Adi' and 'Zelig' banana bunches.
Figure 8:
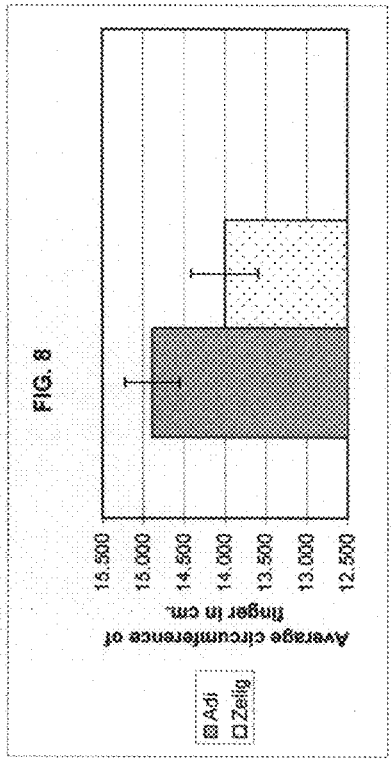
FIG. 8 shows average finger circumference of 'Adi' and 'Zelig'.
Figure 5:
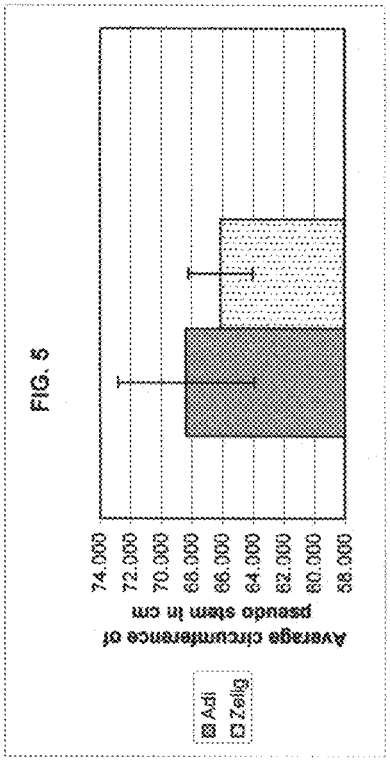
FIG. 5 shows average circumference of pseudo-stem (cm) of 'Adi' and 'Zelig' banana plants.
Figure 7:
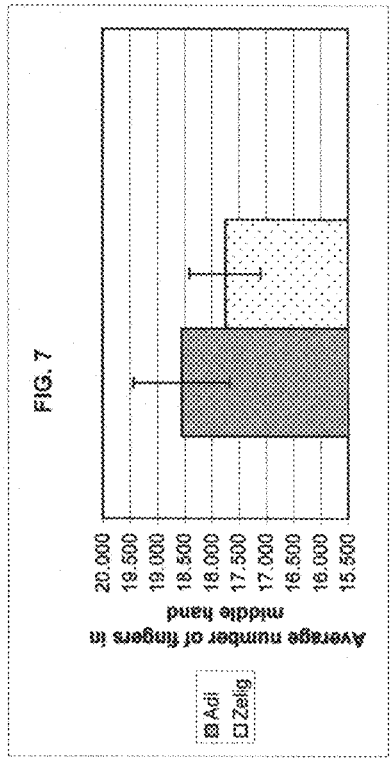
FIG. 7 shows average number of fingers in the middle hand 'Adi' and 'Zelig' banana bunches.
Figure 9:
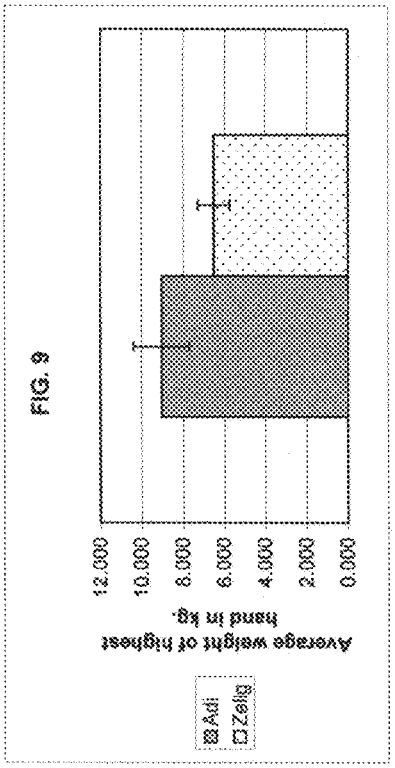
FIG. 9 shows average weight (kg) of upper hand of 'Adi' and 'Zelig' banana plants.

The most apparent distinguishing morphological feature between 'Adi' and its originator 'Zelig' is the plant height as shown in FIG. 1. Other known 'Cavendish' selections range in height between 3.5–4.5 m while the average height of 'Adi' is only 2.14 m. It is well known to those of ordinary skill in the art that dwarf bananas of a given variety will have a reduced bunch weight and shorter finger length. In this case 'Adi' plants have a 17% higher bunch weight as seen in FIG. 2. The weight of the middle hand is an accepted representation of the total weight without taking into count the fruit petiole. FIG. 3 shows a 22% higher weight in the middle hand for 'Adi' in comparison to 'Zelig'. An important quality parameter is finger length. 'Adi''s fingers are approximately 11% longer than 'Zelig' as seen in FIG. 4. In addition, FIG. 8 shows the circumference of each finger in 'Adi' is approximately 1 cm longer (14.9 cm for 'Adi' and 14 cm for 'Zelig'). As shown in FIG. 5, 'Adi''s pseudostem circumference is larger than 'Zelig', although there is a large deviation in the circumference for the individual iterations of the experimental plot in each of the varieties. FIG. 6 shows an equal number of hands in 'Adi' and 'Zelig'. FIG. 7 shows that the average number of fingers in a hand is 23% higher in 'Adi' in comparison to 'Zelig'. It is common practice to remove the lowest hand in the bunch prior to fruit fill in the field due to its short finger length. In the case of 'Adi', the lowest hand weighed 23% more than 'Zelig' as shown in FIG. 9. The upper hand on the bunch is often used as a parameter for fruit size in quality control. The upper hand of 'Adi' FIG. 10, was approximately 28% higher in 'Adi' compared to 'Zelig'. The average weight of the middle finger in the middle hand was 312.5 g for 'Adi' and 264.8 g for 'Zelig'.

An important parameter in fruit quality is the amount of starch in unripe fruit and sucrose in ripening and ripe fruit. The amount of sucrose (FIG. 11) is similar between 'Adi' and 'Zelig' until stage 2 (color change) and increased to a significantly higher level in stage 3 (ripe fruit). The concentration of starch is higher in 'Adi' throughout the ripening process (stages 1–3) when compared to 'Zelig'.

Figure 14:
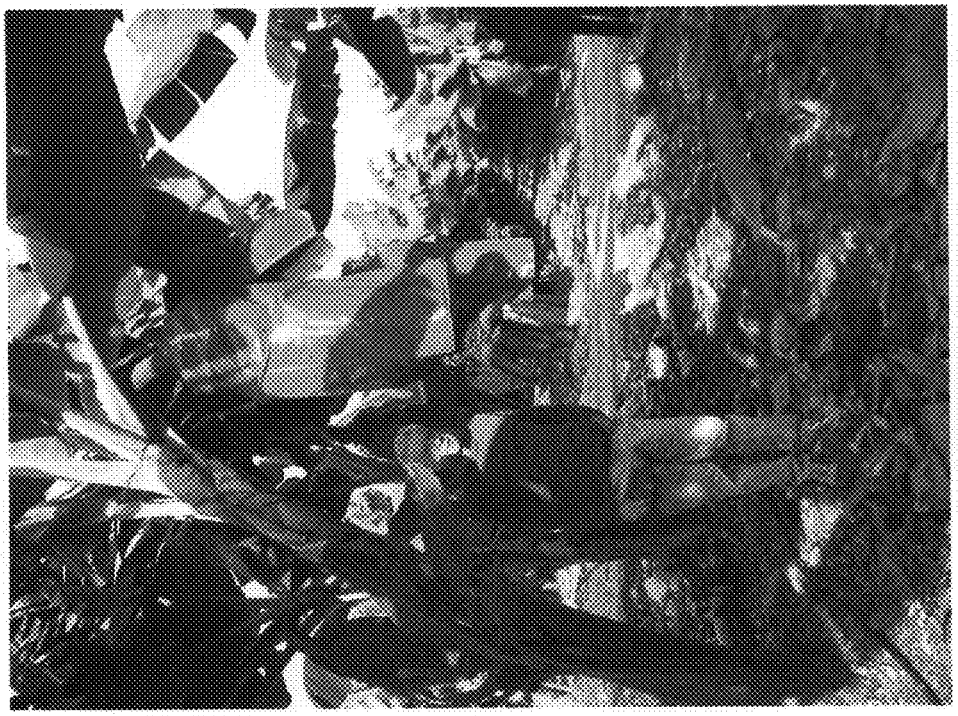
FIG. 14 shows a 'Zelig' banana plant banana plant approximately one month prior to harvesting. Note the difference in height between 'Adi' and 'Zelig'. 'Adi' is much shorter at the same stage of growth grown adjacent to each other.
Figure 13:
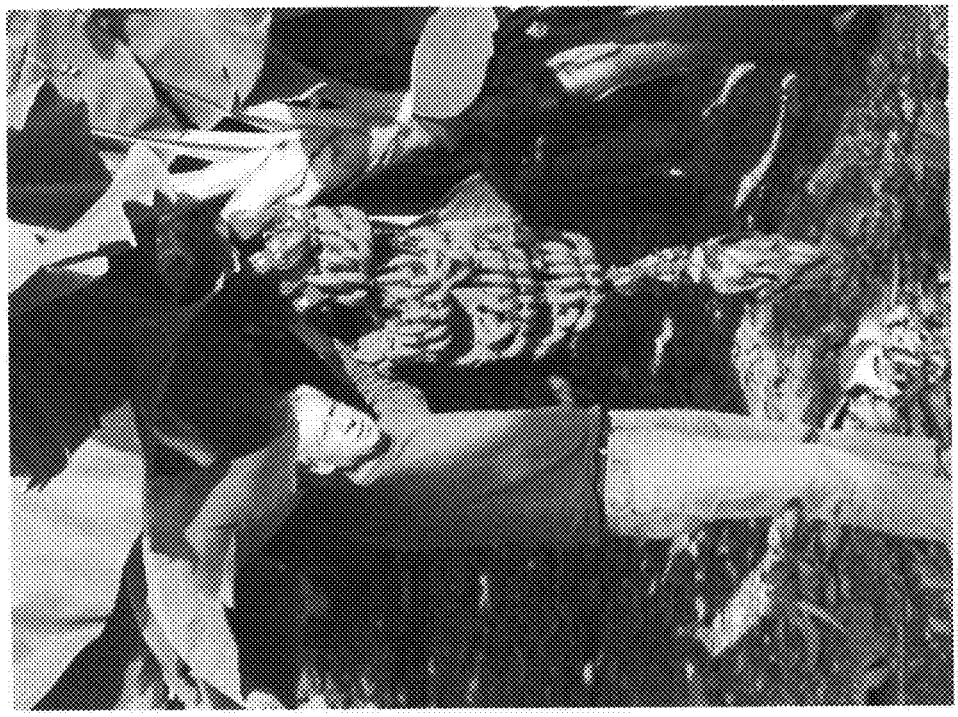
FIG. 13 shows a typical 'Adi' banana plant including a fruit bunch approximately one month prior to harvesting.

The accompanying photographic reproductions show typical specimens of the new banana selection 'Adi' and its originator 'Zelig'. FIG. 13 and FIG. 14 are photos of 'Adi' and 'Zelig' respectively and illustrate the difference in height between them.

'Adi' plants were propagated by tissue culture. The protocol for asexual propagation of 'Adi' is as detailed above in paragraph [0002] steps i. through vii; with the exception that for further propagation after the mutant was created, only 5 steps of subcultures were used instead of the 24 steps as specified above.

BRIEF DESCRIPTION OF THE FIGURES

FIG. 1: Average height (cm) of 'Adi' and 'Zelig' banana plants (*Musa acuminata* AAA, cv. 'Cavendish') measured after completion of flowering. Banana plants were grown under a net in a commercial field in the Western Galilee, Israel. Measurements were performed at harvest of the second cycle of production (20 months after planting) in December 2006. Values represent the average height from soil level to the bent neck of the fruit bunch from 35 plants from each of the selections 'Adi' and 'Zelig'±standard error. Fertigation and other cultural applications were carried out according to commercial banana plantation practices in the Western Galilee, Israel.

FIG. 2: Average bunch weight (Kg) of 'Adi' and 'Zelig' banana (*Musa acuminata* AAA, cv. 'Cavendish') fruit Banana plants were grown under a net in a commercial field in the Western Galilee, Israel. Measurements were performed at harvest of the second cycle of production (20 months after planting) in December 2006. Values represent the average weight of the third 4–5 counting from the top (basipatally) from 35 bunches in each of the selections 'Adi' and 'Zelig'±standard error. Fertigation and other cultural applications were carried out according to commercial banana plantation practices in the Western Galilee, Israel.

FIG. 3: Average weight (Kg) of the middle "fruit-hand" of 'Adi' and 'Zelig' banana (*Musa acuminata* AAA, cv. 'Cavendish') fruit. Banana plants were grown under a net in a commercial field in the Western Galilee, Israel. Measurements were performed at harvest of the second cycle of production (20 months after planting) in December 2006. Values represent the average weight of the third 4–5 counting from the top (basipatally) from 35 bunches in each of the selections 'Adi' and 'Zelig'±standard error. Fertigation and other cultural applications were carried out according to commercial banana plantation practices in the Western Galilee, Israel.

FIG. 4: Average finger length in cm of 'Adi' and 'Zelig' banana fruit. Banana plants (*Musa acuminata* AAA, cv. 'Cavendish') were grown under a net in a commercial field in the Western Galilee Israel. Measurements were performed at harvest of the second cycle of production (20 months after planting) in December 2006. Values represent the average weight of fingers from 35 bunches in each of the selections 'Adi' and 'Zelig'±standard error. Fertigation and other cultural applications were carried out according to commercial banana plantation practices in the Western Galilee, Israel.

FIG. 5: Average circumference of pseudo-stem (cm) of 'Adi' and 'Zelig' banana plants (*Musa acuminata* AAA, cv. 'Cavendish') measured after completion of flowering. Banana plants were grown under a net in a commercial field in the Western Galilee, Israel. Measurements were performed at harvest of the second cycle of production (20 months after planting) in December 2006. Values represent the average circumference at soil level of the pseudo-stems of 35 plants from each of the selections 'Adi' and 'Zelig'±standard error. Fertigation and other cultural applications were carried out according to commercial banana plantation practices in the Western Galilee, Israel.

FIG. 6: Average number of "hands" on bunches of 'Adi' and 'Zelig' banana (*Musa acuminata* AAA, cv. 'Cavendish') selections. Banana plants were grown under a net in a commercial field in the Western Galilee, Israel. Measurements were performed at harvest of the second cycle of production (20 months after planting) in December 2006. Values represent the average number of hands from 35 plants in each of the selections 'Adi' and 'Zelig'±standard error. Fertigation and other cultural applications were carried out according to commercial banana plantation practices in the Western Galilee, Israel.

FIG. 7: Average number of fingers in the middle hand (see legend to FIG. 2) of 'Adi' and 'Zelig' banana (*Musa acuminata* AAA, cv. 'Cavendish') fruit at time of harvest. Banana plants were grown under a net in a commercial field in the Western Galilee, Israel. Measurements were performed at harvest of the second cycle of production (20 months after planting) in December 2006. Values represent the average finger length from 35 plants in each of the selections 'Adi' and 'Zelig'±standard error. Fertigation and other cultural applications were carried out according to commercial banana plantation practices in the Western Galilee, Israel.

FIG. 8: Average finger circumference (cm) of 'Adi' and 'Zelig' banana (*Musa acuminata* AAA, cv. Cavendish) fruit at time of harvest. A representative finger was selected from middle hand as indicated in FIG. 2. The middle finger in the lower row of fruit was sampled for the measurements. Banana plants were grown under a net in a commercial field in the Western Galilee, Israel. Measurements were performed at harvest of the second cycle of production (20 months after planting) in December 2006. Values represent the average finger length from 35 plants in each of the selections 'Adi' and 'Zelig'±standard error. Fertigation and other cultural applications were carried out according to commercial banana plantation practices in the Western Galilee, Israel.

FIG. 9: Average weight (Kg) of highest hand on a bunch of banana (*Musa acuminata* AAA, cv. Cavendish) selections 'Adi' and 'Zelig'. Banana plants were grown under a net in a commercial field in the Western Galilee, Israel. Measurements were performed at harvest of the second cycle of production (20 months after planting) in December 2006. Values represent the average hand weight from 35 plants in each of the selections 'Adi' and 'Zelig'±standard error. Fertigation and other cultural applications were carried out according to commercial banana plantation practices in the Western Galilee, Israel.

Figure 10:
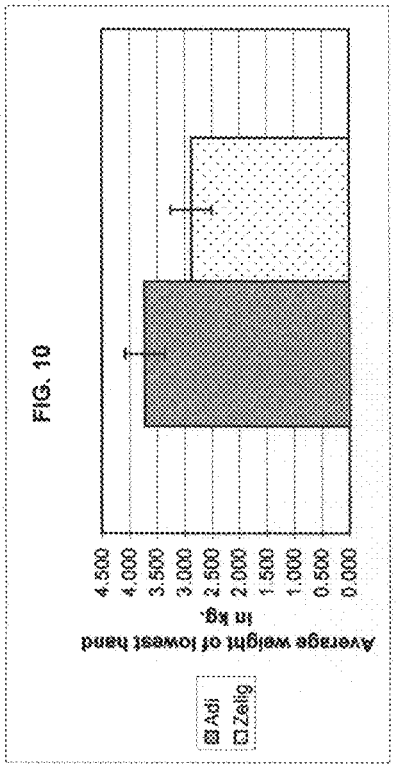
FIG. 10 shows average weight (kg) of lowest hand of 'Adi' and 'Zelig' banana plants.

FIG. 10: Average weight (Kg) of lowest hand on a bunch of banana (*Musa acuminata* AAA, cv. 'Cavendish') selections 'Adi' and 'Zelig'. Banana plants were grown under a net in a commercial field in the Western Galilee, Israel. Measurements were performed at harvest of the second cycle of production (20 months after planting) in December 2006. Values represent the mean hand weight from 35 plants in each of the selections 'Adi' and 'Zelig'±standard error. Fertigation and other cultural applications were carried out according to commercial banana plantation practices in the Western Galilee, Israel.

Figure 11:
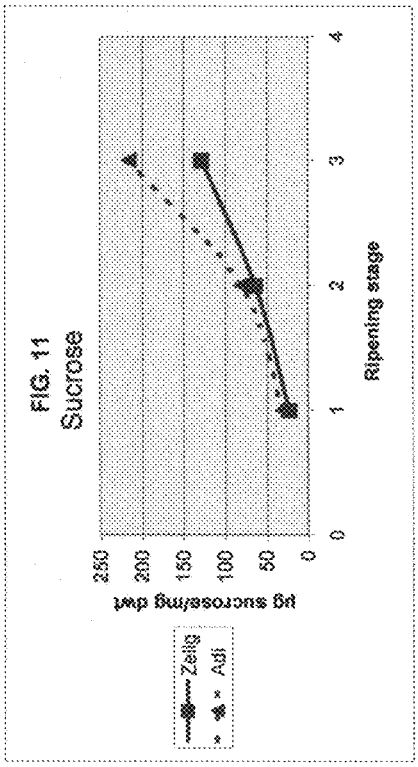
FIG. 11 shows sucrose concentration in μg/mg dry weight.

FIG. 11: Sucrose concentration in μg/mg dry weight. Sugar content was examined in three stages of ripening:

Stage 1—green fruit

Stage 2—approximately half the peel is yellow (color break)

Stage 3—yellow fruit

The pulp of the middle finger from middle hand was sliced in the center (2–3 g slices) and placed in a hot-air oven, set at 80° C., for 48 hrs prior to sugars extraction and analysis. The KOH/ resorcinol method was used for sucrose analysis as described earlier (Khayat Zieslin, 1986, Van Handel, 1968). Data points represent the mean of 15 bunches.

Figure 12:
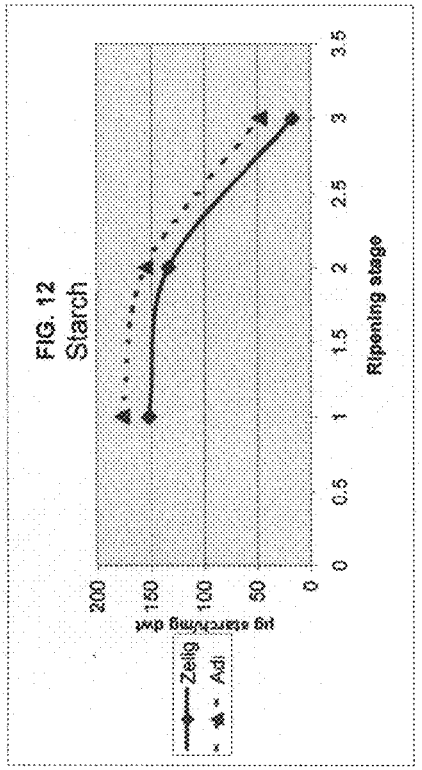
FIG. 12 shows starch concentration in μg/mg dry weight.

FIG. 12: Starch concentration in μg/mg dry weight. Starch content was examined in three stages of ripening:

Stage 1—green fruit

Stage 2—approximately half the peel is yellow (color break)

Stage 3—yellow fruit

The pulp of the middle finger from middle hand was sliced in the center (2–3 g slices) and placed in a hot-air oven, set at 80° C., for 48 hrs prior to starch analysis. Starch content was analyzed according to a method described earlier (Khayat Zieslin, 1986, Van Handel, 1968). Data points represent the mean of 15 bunches.

FIG. 13: Photos of 'Adi', 20 months from planting in the field in the Western Galilee, Israel. The plants were cultivated in a commercial banana plantation and received the same practice of fertigation and desuckering as in FIG. 14. All treatments were in accordance to normal banana growing practices in the Western Galilee, Israel. Photo was taken on December 18, 2007.

FIG. 14: Photos of 'Zelig', 20 months from planting in the field in the Western Galilee, Israel. The plants were cultivated in a commercial banana plantation and received the same practice of fertigation and desuckering as in FIG. 13. All treatments were in accordance to normal banana growing practices in the Western Galilee, Israel. Photo was taken on December 18, 2007.

BRIEF SUMMARY OF THE INVENTION

In the present invention we describe a distinct elite 'Cavendish' selection, 'Adi', that combines dwarf-like stature, wider girth size, higher fruit yield, longer fruit ("fingers") and higher sugar content in the pulp.

DETAILED BOTANICAL DESCRIPTION

Detailed botanical description of the new and distinct selection 'Adi', which includes its general appearance, pseudostem and suckers, petiole, midrib, leaf, inflorescence and male bud, flower bract, male flower, and fruit. This description is based on observations of specimens grown in the Western Galilee, Israel, 20 months after planting. The plantation is at 30 m above sea level, approximately 1200 m East of the Mediterranean sea, adjacent to the town of Shlomi. The description is based on an observation of approximately 50 plants grown in a commercial plantation. Data was collected in December 2006. The descriptors presented herein are in accordance with and include all of the 117 international standards found in "Descriptors for Banana (*Musa* spp.)" elaborated by CIRAD/INIBAP/IPGRI. The color terminology is in accordance with The U.K.'s Royal Horticultural Society's Colour Chart, 2001. Ploidy: Triploid(AAA). Leaf habit: Drooping.

Pseudostem:

*Height.*—2.2 m, measured from the ground to the highest part of the plant at the point where the petiole curves downward.

*Aspect.*—The leaves generated faster than the 'Zelig' selection.

*Pseudostem color.*—Light Green (144-A).

*Appearance.*—Dull (waxy).

*Predominant underlying color of the pseudostem.*—Light Green (145-A).

*Pigmentation of the underlying pseudostem.*—Red-Purple (N59-A).

*Sap color.*—Watery.

*Wax on leaf sheaths.*—Very waxy.

*Number of suckers.*—6.

*Position of suckers.*—Close to parent (vertical growth).

Petiole:

*Lenticels at petiole base.*—Approximately 1 cm wide.

*Lenticel color.*—Brown (200-B).

*Petiole canal leaf III.*—Open with margins spreading.

*Petiole margins.*—Winged and clasping the pseudostem.

*Wing type.*—Dry.

*Petiole wing color.*—Grey-brown (199-D).

*Petiole margin color.*—Green (143-C).

*Edge of petiole margin.*—Very light green-translucent.

*Petiole margin width.*—8 to 13 mm.

Leaf blade:

*Length.*—176–201 cm.

*Leaf blade width.*—64–85 cm.

*Petiole length.*—48–67 cm.

*Color of leaf upper surface.*—Green (137-A).

*Appearance of leaf upper surface.*—Shiny.

*Color of leaf lower surface.*—Green (137-B).

*Appearance of leaf lower surface.*—Dull.

*Wax on leaves.*—Moderately waxy.
*Insertion point of leaf blades on petiole.*—Symmetrical.
*Shape of leaf blade base.*—Tapered in first leaves going to both rounded in later leaves.
*Leaf corrugation.*—Few stripes.
*Color of midrib dorsal surface.*—Green (138-B).
*Color of midrib ventral surface.*—Yellow-Green (146-D).
*Color of cigar leaf dorsal surface.*—Green (143-A).
*Lenticels on leaves of water suckers.*—No lenticels.
*Venation pattern.*—Parallel venation in the leaf lamina in the pinnate style.
*Leaf Shape.*—Oblong with rounded ends.

Inflorescence/male bud:
*Peduncle length.*—65–70 cm.
*Empty nodes on peduncle.*—Two or more.
*Peduncle width.*—6.5–7.5 cm.
*Peduncle color.*—Yellow-green (144-A).
*Peduncle hairiness.*—Hairless.

Rachis: Present.
*Position.*—Falling vertically.
*Male bud shape.*—Ovoid.
*Male bud size.*—24–28 cm.
*Average diameter of male bud.*—17 cm.

Bract:
*Bract base size.*—Average 11 cm. for the part connected to the rachis.
*Bract apex shape.*—Obtuse.
*Bract length.*—Average 29 cm. at longest point.
*Bract width.*—Average 22 cm. at the widest point.
*Color of the bract external face.*—Red-purple (59-A).
*Color of the bract internal face.*—Grayed-orange (176-A).
*Color stripes on bract.*—With discolored lines on the external face.
*Bract scars on rachis.*—Not prominent.
*Male bract shape.*—Ovate.
*Wax on the bract.*—Moderately waxy.
*Presence of grooves on the bract.*—Moderate.

Male flower: Data taken at completion of flower emergence.
*Male flower behavior.*—Falling before the bract.
*Compound tepal basic color.*—Red-purple (65-A), later becoming grey and black.
*Lobe color of compound tepal.*—Yellow (8-A).
*Free tepal appearance.*—Corrugated.
*Style shape.*—Straight.
*Stigma color.*—Orange (25-C).
*Ovary basic color.*—Yellow (8-D).
*Ovary pigmentation.*—Very few signs of pigmentation.

Fruit position: Curved upward.
*Apex.*—Somewhat rounded.
*Number of fruit per hand.*—18.5 average.
*Fruit length.*—20.4 cm. average.
*Fruit shape longitudinal curvature.*—Slightly curved.
*Fruit circumference.*—14.8 cm. average.
*Fruit pedicel length.*—3.8 cm. average.
*Pedicel surface.*—Hairless.
*Immature fruit peel color.*—Green (144-A).
*Mature fruit peel color.*—Yellow (14-C).
*Fruit peel thickness.*—2.0 mm.
*Adherence of the fruit peel.*—Fruit peels easily.
*Cracks in fruit peel.*—Without cracks.
*Pulp in fruit.*—With pulp.
*Pulp color before maturity.*—White (155-D).
*Pulp color at maturity.*—(155-D).
*Fruit is eaten.*—Ripe.
*Flesh texture.*—Firm.
*Predominant taste.*—Sweet.
*Main use.*—Dessert banana.
*Presence of seed.*—No seeds.

Agronomic characteristics: averages taken during 2005–2006 for second crop in a plot of 1800 plants per hectare:
*Number of leaves at flowering.*—14. Average bunch weight 47.3 kg.
*Number of hands.*—9.
*Finger length.*—Average 20.4 cm.
*Average number of fingers per hand.*—18.6.

It is claimed:

1. 'Adi', a new and distinct selection of banana plant, substantially as illustrated and described, which is a dwarf stature plant, with wider girth size, higher fruit yield, longer fruit ("fingers") and higher sugar content in the pulp.

* * * * *

Starch

Sucrose

"Zelig"

"Adi"